United States Patent [19]
Fujii et al.

[11] Patent Number: 6,121,329
[45] Date of Patent: *Sep. 19, 2000

[54] TOPICAL ADMINISTRATION OF 2-AMINO-2-(2-(4-OCTYLPHENYL)ETHYL)PROPANE-1,3-DIOL

[75] Inventors: Tsuneo Fujii; Tadashi Mishina, both of Fukuoka; Koji Teshima, Saitama; Tomonori Imayoshi, Fukuoka, all of Japan

[73] Assignee: Yoshitomi Pharmaceutical Industries, Ltd., Osaka-fu, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,728

[22] PCT Filed: Dec. 24, 1996

[86] PCT No.: PCT/JP96/03757

§ 371 Date: Aug. 27, 1997

§ 102(e) Date: Aug. 27, 1997

[87] PCT Pub. No.: WO97/24112

PCT Pub. Date: Jul. 10, 1997

[30] Foreign Application Priority Data

Dec. 28, 1995 [JP] Japan ..................... 7-342503

[51] Int. Cl.$^7$ ................. A61K 33/24; A01N 59/16
[52] U.S. Cl. ............... 514/653; 424/400; 424/45; 424/427; 424/443; 514/885; 514/886; 514/912; 514/946; 514/947; 514/966; 514/969
[58] Field of Search .................... 514/653, 649, 514/886, 885, 912, 946, 947, 966, 969; 424/400, 443, 427, 45

[56] References Cited

U.S. PATENT DOCUMENTS

| | | |
|---|---|---|
| 5,011,844 | 4/1991 | Fehr . |
| 5,504,068 | 4/1996 | Komiya et al. . |
| 5,604,229 | 2/1997 | Fujita et al. . |

FOREIGN PATENT DOCUMENTS

| | | |
|---|---|---|
| 0501579 A1 | 9/1992 | European Pat. Off. . |
| 0550006 A2 | 7/1993 | European Pat. Off. . |
| 0550008 A2 | 7/1993 | European Pat. Off. . |
| 0694308 A1 | 1/1996 | European Pat. Off. . |
| 94/089943 | 4/1994 | WIPO . |

OTHER PUBLICATIONS

Adachi et al., Design, Synthesis & Structure–Activity Relationships of 2–substituted–2–amino–1,3–propanediols: Discovery of a Novel Immunosuppressant, FTY 720, Bioorganic & Medicinal Chemistry Letters, vol. 5, No. 8, pp. 853–856, Apr. 20, 1995.

Fujita et al., Bioorganic & Medicinal Chemistry Letters, vol. 5, No. 8, 847–852 (1995).

JP 07–188046, A (LTT Institute Co., Ltd.) Jul. 25, 1995 (abstract only).

JP 06–256182, A (LTT Institute Co., Ltd.) Sep. 13, 1994 (abstract only).

*Primary Examiner*—Thurman K. Page
*Assistant Examiner*—Brian K. Seidleck
*Attorney, Agent, or Firm*—Birch, Stewart, Kolasch & Birch, LLP

[57] ABSTRACT

An external preparation for topical administration which aims at inhibiting rejection reactions at organ or bone marrow transplantation or treating autoimmune diseases or allergic diseases and contains as the active ingredient 2-amino-2-(2-(4-octylphenyl)ethyl)propane-1,3-diol or a pharmaceutically acceptable acid addition salt thereof.

22 Claims, No Drawings

TOPICAL ADMINISTRATION OF 2-AMINO-2-(2-(4-OCTYLPHENYL)ETHYL)PROPANE-1,3-DIOL

This application is a 371 of PCT/JP96/03757, filed Dec. 24, 1996.

TECHNICAL FIELD

This invention relates to an external preparation 2-Amino-2-(2-(4-Octylphenyl)Ethyl)Propane-1,3-Diol Or Pharmaceutically Acceptable Salts Thereof For Topical Administration for topical administration, in more detail to an external preparation for topical administration which contains as the active ingredient 2-amino-2-(2-(4-octylphenyl)ethyl)propane-1,3-diol or pharmaceutically acceptable acid-addition salts thereof.

BACKGROUND ART

WO94/08943 discloses 2-aminopropane-1,3-diol compounds which are useful as immunosuppressive agents. Among those compounds, 2-amino-2-(2-(4-octylphenyl)ethyl)propane-1,3-diol hydrochloride (hereunder sometimes referred to as Compound (I)) is under research and development for the transplantation of organs and autoimmune diseases. In order to inhibit rejection reaction at organs or bone marrow and treat autoimmune diseases and allergic diseases, drugs are usually applied topically to the affected parts in addition to the oral administration. Then, it has been desirable to develop the pharmaceutical preparations of Compound (I) which can be administered through the skin, eye, lung, bronchus, nose or rectum.

DISCLOSURE OF THE INVENTION

From the point of view as above, the present inventors have made intensive investigations for the development of a pharmaceutical preparation of Compound (I) which can be administered through the skin, eye, lung, bronchus, nose or rectum, and have succeeded in formulating such pharmaceutical preparation and thereby completed the present invention.

Namely, the present invention relates to an external preparation for topical administration which contains as the active ingredient 2-amino-2-(2-(4-octylphenyl)ethyl)propane-1,3-diol or pharmaceutically acceptable acid-addition salts thereof (hereunder sometimes referred to as the compound of the present invention).

The compound of the present invention may be prepared in accordance with the methods described in WO94/08943.

The pharmaceutically acceptable acid-addition salts are inclusive of a salt with an inorganic acid such as hydrochloride, hydrobromide or sulfate, or a salt with an organic acid such as acetate, fumarate, maleate, benzoate, citrate, malate, methanesulfonate or benzenesulfonate, preferably hydrochloride. The present invention embraces the hydrate or solvate of the compound of the present invention.

The external preparation for topical administration which is applicable to the compound of the present invention includes an ointment, a paste, a liniment, a lotion, a plaster, a cataplasm, an eye drop, an eye ointment, a suppository, a fomentation, an inhalant, a spray, an aerosol, a paint, a nasal drop, a cream, a tape, a patch and the like.

The external preparation for topical administration of the present invention contains the compound of the present invention in a form of a mixture with an organic or inorganic carrier or excipient, and, for example, can be used in a form a solid, semi-solid or solution pharmaceutical preparation.

The compound of the present invention can be mixed with, for example, a non-toxic and pharmaceutically acceptable carrier which is usually employed for obtaining an external preparation for topical administration.

A carrier which can be used includes water, glucose, lactose, arabic gum, gelatin, mannitol, starch paste, magnesium trisilicate, talc, corn starch, keratin, colloid silica, potato starch, urea and other carriers which are suitable for preparing a solid, semi-solid or solution composition. Further, an adjuvant, a stabilizer, a thickener, a coloring matter or a flavoring agent can be added.

The compound of the present invention as an active ingredient of the external preparation for topical administration of the present invention can be contained in an amount enough to exhibit the desired activity depending on the symptom or severity of the diseases. In the case of the treatment of the symptom and diseases induced from immune disorder as mentioned below, the compound of the present invention can be administered by way of a topical administration, an aerosol or a rectal administration in a form of a dosage unit composition which contains pharmaceutically acceptable and non-toxic carrier, adjuvant and excipient. In the treatment of reversible obstructive airways disease, the compound of the present invention is preferably administered to lung by an aerosol in a form of, particularly a powder or a solution.

The amount of the compound of the present invention which can be mixed with a carrier can vary depending on the host to be treated and a specified dosage form. The specified dose of the specified patient should be determined depending on the various factors such as age, body weight, the whole condition of health, sex, meal, time for administration, administration route, rate of excretion, combination of drug and the severity of the specified diseases under treatment.

The external preparation for topical administration containing the compound of the present invention will be explained in more detail as follows:

When the compound of the present invention is used in the form of an ointment, it is contained in an amount of 0.01 to 10 w/w % in the ointment.

The ointment base which can be used includes oleaginous base (a natural wax such as white beeswax or carnauba wax, a petroleum wax such as solid paraffin or microcrystalline wax, a hydrocarbon wax such as liquid paraffin, white soft paraffin or yellow petrolatum, plastibase, zelen 50W, silicone, a vegetable oil, pork tallow, beef tallow, a simple ointment or lead oleate plaster), an emulsion type ointment base (an O/W type base such as a hydrophilic ointment or a vanishing cream or a W/O type base such as a hydrophilic petrolatum, a purified lanolin, aquahole, eucelin, neocelin, an absorptive ointment, a hydrated lanolin, cold cream, a hydrophilic plastibase), a water-soluble base (a macrogol ointment or solbase) or a suspension type ointment base (a lyogel base, i.e. a hydrogel base such as a non-fat ointment, a gelbase or lotion; or an FAPG base (a suspension of a microparticle of an aliphatic alcohol such as stearyl alcohol or cetyl alcohol in propylene glycol), and these ointment base can be used alone or in a combination of not less than two bases.

Further, when to be used as an ointment, the compound of the present invention is dissolved in a solubilizing and absoptive accelerating agent and added to the above-mentioned ointment base.

The solubilizing and absoptive accelerating agent to be used means the agent in which the compound of the present invention is soluble at a concentration of at least not less than 0.01 w/w % and which can accelerate the absorption of the compound of the present invention from skin when formulated as an ointment, and includes a lower alkanediol (e.g. ethylene glycol, propylene glycol or butylene glycol), an alkylene carbonate (e.g. propylene carbonate or ethylene carbonate), an alkanedicarboxylic acid ester (e.g. dimethyl adipate, diethyl adipate, diisopropyl adipate, diethyl pimerate, diethyl sebacate or dipropyl sebacate), a higher alkanoic acid glycerin ester (e.g. monolaurin, dilaurin or trilaurin), a higher alkenoic acid glycerin ester (e.g. monoolein, diolein or triolein), a higher alkanoic acid alkyl ester (e.g. isopropyl myristate or ethyl myristate), a higher unsaturated alcohol (e.g. geraniol or oleyl alcohol) or an azacycloalkane (e.g. 1-dodecylazacycloheptan-2-one). These solubilizing and absoptive accelerating agent can be used alone or in a mixture of not less than two agents, and can be added at a sufficient amount to dissolve the compound of the present invention. The amount generally ranges from 2 parts by weight to 200 parts by weight per one part by weight of the compound of the present invention. The upper amount is limited not to deteriorate the physicochemical properties of the ointment.

The ointment which contains the compound of the present invention may contain, in addition to the above-mentioned ointment base, other additives such as an emulsifier (e.g. polyoxyethylene hardened caster oil, glycerol monostearate, sorbitan sesquioleate or lauromacrogol); a suspending agent (e.g. polyoxyethylene glycol, polyvinylpyrrolidone or sodium carboxymethylcellulose); an antioxidant (e.g. a phenol or a quinone); a preservative (e.g. paraoxybenzoic acid ester); a humectant (e.g. glycerin, D-sorbitol or propylene glycol); a favoring agent, a coloring matter; an antiseptic; a higher alkenoic acid (e.g. oleic acid), and moreover other drugs which are useful for the treatment of a skin diseases.

The ointment of the present invention can be prepared by mixing a solution containing the compound of the present invention with an ointment base in accordance with a conventional method. In the process of formulation, not less than one of the adjuvant or additive mentioned above can be simultaneously added to the ointment base. Furthermore, the ointment can be manufactured by dissolving the compound of the present go invention in the solubilizing and absoptive accelerating agent, admixing the obtained solution with the ointment base, stirring the obtained mixture under heating, and then cooling the resultant mixture.

The ointment containing the compound of the present invention can be used by applying to the affected part of the skin once to several times (e.g. once to four times) a day.

The paste or liniment containing the compound of the present invention can be prepared by using the same base and according to the same method as those of the ointment as mentioned above.

The lotion containing the compound of the present invention means a minute and homogeneous suspension or partial solution of the active ingredient compound in a liquid medium, and an emulsifier can be added thereto.

In case that the compound of the present invention is used as a lotion, the content may be adjusted to 0.01 to 10 w/w % in the lotion.

The liquid medium to be used in the lotion containing the compound of the present invention includes water, a lower alcohol, a glycol, glycerin or a mixture thereof. Among them, all of the lower alcohols which do not decompose the active ingredient and are not irritant to skin can be used, and are inclusive methanol, ethanol, isopropyl alcohol, propanol or butanol. The glycol includes ethylene glycol, propylene glycol, butylene glycol or mono lower ethers thereof. Among these liquid media, water, the lower alcohol or a mixture thereof are most preferable because these media improve the absorption of the active ingredient to the skin. The amount of these liquid media preferably ranges from 5 parts by weight to 1,000 parts by weight per one part by weight of the compound of the present invention.

Further, to the lotion containing the compound of the present invention may be added a solubilizing and absoptive accelerating agent in which the compound of the present invention is soluble at a concentration of at least not less than 0.01 w/w % and which can accelerate the absorption of the compound of the present invention from skin when formulated as a lotion, and includes an alkanedicarboxylic acid ester (e.g. dimethyl adipate, diethyl adipate, diisopropyl adipate, diethyl pimerate, diethyl sebacate or dipropyl sebacate) or a higher alkanoic acid alkyl ester (e.g. isopropyl myristate or ethyl myristate). These solubilizing and absoptive accelerating agent can be used alone or in a mixture of not less than two agents. The amount generally ranges from 5 parts by weights to 5,000 parts by weights per one part by weight of the compound of the present invention. The content of the solubilizing and absoptive accelerating agent is desirably in the range of 1 to 30 w/w %.

The emulsifier for the lotion containing the compound of the present invention is employed for the purpose of suspending an insoluble medicine minutely and homogeneously in an aqueous solution, and should be non-toxic to human beings, and includes a pharmaceutically acceptable natural emulsifier and synthetic emulsifier.

Various emulsifiers which are derived from animals and vegetables can be used as the natural emulsifier, and include egg lecithin, soybean lecithin or a hydrogenated product thereof, phosphatidyl choline, sphingomyelin, arabic gum or gelatin. Cationic, anionic or non-ionic surfactants can be used as the synthetic emulsifier, and preferably include a castor oil surfactant, especially an HCO (polyoxyethylene hardened castor oil) such as HCO-60, HCO-50 or HCO-40. Further, a polyoxyethylenesorbitan aliphatic acid ester such as polysorbate 80, a glycerin aliphatic acid ester such as glycerin monocaprylate, a polyoxyethylene aliphatic acid ester such as polyoxyethylene 40 monostearate, a middle chain aliphatic acid mono(or di)glyceride (e.g. $C_6$–$C_{12}$ aliphatic acid mono(or di)glycerides such as caprylic acid diglyceride, caprylic acid monoglyceride or caproic acid diglyceride) or a polyoxyethylated glyceride such as polyoxyethylated oleic acid glyceride.

The above-mentioned emulsifiers can be used as the primary emulsifier, and, if necessary, in combination with an auxiliary emulsifier. The auxiliary emulsifier is conventional and non-toxic to human beings, and includes cholesterol, agar, magnesium hydroxide, methylcellulose or pectin.

These primary emulsifier and auxiliary emulsifier may be used each alone or in combination of two or more of them, respectively.

The emulsifier is contained in the lotion of the present invention in an amount being able to emulsify the compound of the present invention and other additives to be contained, and preferably ranges from 0.1 part by weight to 10 parts by weight per one part by weight of the compound of the present invention.

In order to increase the viscosity, a viscosity-increasing agent may be added to the lotion of the present invention. The viscosity-increasing agent is any conventional agent which is usually added to give the viscosity to the liquid and is non-toxic to human beings, and includes carboxypolymethylene. The viscosity-increasing agent is used when the lotion with a high viscosity is desired. The content of the viscosity-increasing agent may vary depending on the desired viscosity of the lotion and preferably ranges from 0.01 to 5 w/w %.

The lotion of the present invention may further contain a stabilizer which is used for the stabilization of the active ingredient compound in an aqueous solution, and if necessary, it may further contain other additives which are usually used for the lotion, such as a favoring agent, a coloring matter, an antiseptic or a higher alkenoic acid such as oleic acid, or other drugs which are useful for the treatment of the skin diseases.

The lotion which contains the compound of the present invention may be prepared by a conventional method in this field.

The lotion which contains the compound of the present invention can be used by applying to the affected part of the skin once to several times (e.g. once to four times) a day. When the lotion has a low viscosity, it can be applied by filling the composition of the lotion to a spray vessel and spraying directly to the skin.

In case that the compound of the present invention is used in the form of an eye drop or a nasal drop, the solvent employed includes a sterile distilled water or, in particular a distilled water for injection. The concentration of the active compound usually ranges from 0.01 to 2.0 w/v %, and may be increased or decreased depending on the aim of use.

The eye drop or a nasal drop which contains the compound of the present invention further may contain various additives such as a buffer, an isotonic agent, a solubilizing agent, a preservative, a viscosity-increasing agent, a chelating agent, a pH adjustor or an aromatic.

The buffer includes, for example, a phosphate buffer (e.g. sodium dihydrogen phosphate-disodium hydrogen phosphate or potassium dihydrogen phosphate-dipotassium hydrogen phosphate), a borate buffer (e.g. boric acid-borax), a citrate buffer (e.g. sodium citrate-sodium hydroxide), a tartrate buffer (e.g. tartaric acid-sodium tartrate), an acetate buffer (e.g. acetic acid-sodium acetate), a carbonate buffer (e.g. sodium carbonate-citrate or sodium carbonate-boric acid) or an amino acid (e.g. sodium glutamate or ∈-aminocapronic acid).

The isotonic agent includes a saccharide such as sorbitol, glucose or mannitol, a polyhydric alcohol such as glycerin or propylene glycol, a salt such as sodium chloride or borax, or boric acid and the like.

The solubilizing agent includes a non-ionic surfactant such as polyoxyethylene sorbitan monooleate (polysorbate 80), polyoxyethylene monostearate, polyethylene glycol or polyoxyethylene hardened castor oil and the like.

The preservative includes, for example, a quaternary ammonium salt such as benzalkonium chloride, benzethonium chloride or cetyl pyridinium chloride, a parahydroxybenzoic acid ester such as methyl parahydroxybenzoate, ethyl parahydroxybenzoate, propyl parahydroxybenzoate or butyl parahydroxybenzoate, benzyl alcohol, phenethyl alcohol, sorbic acid or a salt thereof, thimerosal, chlorobutanol, sodium dehydroacetate, methylparaben or propylparaben.

The viscosity-increasing agent includes, for example, polyvinylpyrrolidone, hydroxyethylcellulose, hydroxypropylcellulose, methylcellulose, hydroxypropylmethylcellulose, or carboxymethylcellulose or a salt thereof.

The chelating agent includes disodium edetate or citric acid and the like.

The pH adjustor includes hydrochloric acid, citric acid, phosphoric acid, acetic acid, tartaric acid, sodium hydroxide, potassium hydroxide, sodium carbonate or sodium bicarbonate and the like.

The aromatic includes 1-menthol, borneol, a camphor (e.g. dl-camphor) or eucalyptus oil and the like.

The eye drop which contains the compound of the present invention may be usually adjusted to about 4.0 to about 8.5 of pH, and the nasal drop to about 4.0 to about 8.5 of pH.

The eye drop may contain the compound of the present invention in a sufficient amount to be able to effectively prevent the eye inflammation, which may vary depending on the symptom or the sort of inflammation, and usually ranges from about 5.0 to about 1,000 µg for one administration. It may be administered once to several times (e.g. once to four times) a day.

The aerosol containing the compound of the present invention means a pharmaceutical preparation which can be applied at the time of treatment by spraying a solution or a suspension of the active compound using a pressure of a liquid gas or compressed gas filled in the same vessel or another vessel. The aerosol can be prepared by dissolving the compound of the present invention in a distilled water, and, if necessary, dissolving or suspending the solution in the same solubilizing and adsorptive accelerating agent as above, and, if necessary, adding the additive such as pH adjustor or antiseptic as mentioned above, and then sealing closely with a valve and compressing the propellant. The propellant to be used includes dimethyl ether, liquid natural gas, carbon dioxide, nitrogen gas, a substituted flon gas and other conventional propellants.

The aerosol may further contain a refrigerant such as 1-menthol, a camphor, methyl salicylate and the like.

The inhalant or spray which contains the compound of the present invention can be prepared according to the same methods as those mentioned in aerosol. An inhaler or a nebulizer can be used for inhalant and a spraying vessel can be used for spray.

When the compound of the present invention is used as a suppository, the suppository can be prepared in a conventional manner using a conventional base for the suppository. The compound of the present invention is contained in the suppository in an amount sufficient to exhibit the pharmaceutical effect, which can vary depending on the age or symptom of the patient, and preferably ranges from 0.1 to 60 mg.

The base for suppository of the present invention is the conventional base, and includes an oil and fat from animal and vegetable such as olive oil, corn oil, castor oil, cotton seed oil, oil from wheat with germ, cacao oil, beef tallow, pork tallow, wool tallow, turtle tallow, squalene or a hardened oil, an oil and fat from mineral such as Vaseline, white soft paraffin, solid paraffin, liquid paraffin, dehydrated lanolin or silicon oil, a wax such as hohoba oil, carnauba wax, yellow bees wax or lanolin, or a partially synthetic or totally synthetic glycerin aliphatic acid ester such as mono, di or triglyceride of a middle or higher aliphatic acid such as a straight-chain saturated aliphatic acid (e.g. lauric acid, myristic acid, palmitic acid or stearic acid), or a straight-chain unsaturated aliphatic acid (e.g. oleic acid, linoleic acid or linolenic acid). The commercially available products are exemplified Witepsol [manufactured by Dynamitnobel Co.; a mixture of mono-, di- and tri-glycerides of $C_{12}$–$C_{18}$ saturated aliphatic acid, in more detail, Witepsol H series (e.g. Witepsol H5, H12, H19, H32, H35, H37, H39, H42, H175 or H185), Witepsol W series (e.g. Witepsol W25, W31, W35 or W45), Witepsol E series (e.g. Witepsol E75, E76, E79 or E85) or Witepsol S series (e.g. Witepsol S52, S55 or S58) are included]; Pharmasol (manufactured by Nippon Oils and Fats Co.); Isocacao (manufactured by Kao Co.); SB (manufactured by Kanegafuchi Chemical Co. and Taiyo Yusi Co.; a mixture of mono-, di- and tri-glycerides of $C_{12}$–$C_{18}$ saturated aliphatic acid, in more detail, SB-H, SB-E or SB-AM are included); Nopata (manufactured by Henkel AG.); Sapoyer (manufactured by Gattfords Co.; a mixture of mono-, di- and tri-glycerides of $C_{10}$–$C_{18}$ saturated aliphatic acid, in more detail, Sapoyer NA, Sapoyer OS, Sapoyer AS, Sapoyer BS, Sapoyer BM or sapoyer DM are included); Masaesthalinum (manufactured by Dynamitnobel Co.; a mixture of mono-, di- and tri-glyceride of $C_{10}$–$C_{18}$ saturated aliphatic acid, in more detail, Masaesthalinum A, AB, B, BB, BC, BCF, C, D, E or BD and Masaasthalinum 299 are included); or Migriol 810 or Migriol 812 (manufactured by Dynamitnobel Co.; a mixture of triglycerides of $C_8$–$C_{12}$ saturated aliphatic acid, in more detail, one or more of them may optionally be incorporated when the partially synthetic or totally synthetic glycerin aliphatic acid ester as mentioned above are incorporated). Further, other synthetic products such as polyethylene glycol or polyoxyethylene alcohol can be exemplified. The bases are used in an amount of 25 to 99.9% by weight based on the total weight of the suppository.

To the suppository containing the compound of the present invention may be added, if necessary, a preservative, a stabilizer, a surfantant, an aromatric, a pH adjustor or a purified water.

The suppository containing the compound of the present invention may be in various forms such as a rectal suppository which is solid at the normal temperature and melts at a body temperature; an ointment or liquid enema which can be prepared by dissolving or suspending the compound of the present invention in a liquid base; a soft capsule for the rectal administration; or an injection for the rectal administration.

The external preparation for topical administration of the present invention can be used for the prevention or treatment of various medical indications, which have been already applied by the oral administration of the compound of the present invention, such as immunosuppression in organs or bone marrow transplantation, various autoimmune diseases or various allergy diseases. Namely, the compound of the present invention has pharmacological activities such as immunosuppressive activity or antimicrobial activity and therefore are useful for the prevention or treatment of resistance to transplantation or transplantation rejection of organs or tissues (such as heart, kidney, liver, lung, bone marrow, cornea, pancreas, intestinum tenue, limb, muscle, nervus, fatty marrow, duodenum, skin or pancreatic islet cell etc., including xeno-transplantation), graft-versus-host diseases by bone marrow transplantation (GvHD), autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms.

The active compound is also useful for treating inflammatory, proliferative and hyperproliferative skin diseases and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedemas, vasculitides, erythemas, cutaneous eosinophilias, acne, alopecia areata, eosinophilic fasciitis, and atherosclerosis.

More particularly, the compound of the present invention is useful in hair revitalizing, such as in the treatment of female or male pattern alopecia, or senile alopecia, by providing epilation prevention, hair germination, and/or a promotion of hair generation and hair growth.

The compound of the present invention is further useful in the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (for example late asthma and airway hyperreponsiveness), bronchitis and the like.

The compound of the present invention may also be useful for treating hepatic injury associated with ischemia.

The compound of the present invention is also applied to certain eye diseases such as conjunctivitis, keratoconjunctivitis, keratitis, vernal conjunctivitis, uveitis associated with Behcet's disease, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The compound of the present invention is also useful for preventing or treating inflammation of mucosa or blood vessels (such as leukotriene B4-mediated diseases, gastric ulcers, vascular damage caused by ischemic diseases and thrombosis, ischemic bowel disease, inflammatory bowel disease (e.g. Crohn's disease and ulcerative colitis) necrotizing enterocolitis), or intestinal lesions associated with thermal burns.

Further, the compound of the present invention is also useful for treating or preventing renal diseases including interstitial nephritis, Goodpasture's syndrome, hemolytic uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodosa and myocardosis; collagen disease including scleroderma, Wegener's granuloma and Sjogren'syndrome; adiposis; eosinophilic fasciitis; periodontal disease; nephrotic syndrome; hemolytic uremic syndrome; and muscular dystrophy.

Further, the compound of the present invention is indicated in the treatment of diseases including intestinal inflammations or allergies such as Coeliac disease, proctitis, eosinophilic gastroenteritis, mastocytosis, Crohn's disease or ulcerative colitis; and food related allergic diseases which have symptomatic manifestation remote from the gastrointestinal tract, for example migraine, rhinitis and eczema.

The compound of the present invention also has liver regenerating activity and/or activity in promoting hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compound of the present invention is also indicated for use as antimicrobial agents, and thus may be used in the treatment of diseases caused by pathogenic microorganisms and the like.

Further, the compound of the present invention can be used in the prevention or treatment of malignant rheumatoid arthritis, amyloidosis, fulminant hepatitis, Shy-Drager syndrome, pustular psoriasis, Behcet's disease, systemic lupus erythematosus, endocrine opthalmopathy, progressive systemic sclerosis, mixed connective tissue disease, aortitis syndrome, Wegener's gramulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

Moreover, the compound of the present invention can be used in combination with other immunosuppressant(s), steroid(s) (prednisolone, methylprednisolone, dexamethasone, hydrocortisone and the like) or nonsteroidal anti-inflammatory agent. As the other immunosuppressant, preferred is particularly selected from azathioprine, brequinar sodium, deoxyspergualin, mizoribine, mycophenolate 2-morphorinoethyl, cyclosporin, rapamycin, tacrolimus monohydrate.

BEST MODE FOR CARRYING OUT THE INVENTION

The following pharmaceutical examples are illustrative of the present invention.

Pharmaceutical Preparation 1

2-Amino-2-(2-(4-octylphenyl)ethyl)propane-1,3-diol hydrochloride (hereunder referred to as compound (I), 1 g) was dissolved in 19 g of hydrophilic petrolatum under heating at 60° C., and cooled with stirring to prepare an ointment containing 5% of Compound (I).

Pharmaceutical Preparation 2

Compound (I) (1 g) was mixed well with 19 g of plastibase (gelled hydrocarbon) in a mortar for about 30 minutes to prepare an ointment containing 5% of Compound (I).

Pharmaceutical Preparation 3

To a melted Witepsol H15 (72.47 g) at 40° C. was added Compound (I) (30 mg), and the mixture was stirred to suspend Compound (I). The homogeneous mixture was filled in a container at a weight of 725 mg each to prepare a suppository containing 0.3 mg of Compound (I) in 725 mg.

Pharmaceutical Preparation 4

To a 70 ml of sterile distilled water was added 0.2 g of polyvinylalcohol and it is dissolved by heating at 70° C. with stirring. To the solution was suspended homogeneously 0.1 g of polyoxyethylene hardened castor oil 60, and then the mixture was cooled to room temperature. To the solution were added 0.2 g of Compound (I), 0.5 g of disodium hydrogen phosphate, 0.1 g of sodium dihydrogen phosphate, 0.8 g of sodium chloride and 0.007 g of benzethonium chloride to give a solution. To the solution was added sterile distilled water to prepare an eye drop containing Compound (I) in a total volume of 100 ml.

Pharmaceutical Preparation 5

To 70 ml of sterile distilled water were added 0.4 g of Compound (I), 0.2 g of sodium citrate, 0.1 g of polysorbate 80, 2.6 g of glycerin and 0.007 g of benzethonium choride, and to the solution obtained was added sterile distilled water to prepare a nasal drop containing Compound (I) in a total volume of 100 ml.

Pharmaceutical Preparation 6

To 100 mg of Compound (I) were added 1 ml of isopropyl myristate and 4 ml of ethanol at room temperature to prepare a lotion containing 2% of Compound (I).

Industrial Applicability

The external preparation containing the compound of the present invention is a useful topical preparation for inhibiting the rejection reactions at organ or bone marrow transplantation or treating the autoimmune diseases or allergic diseases.

What is claimed is:

1. A method for treating a disease or disorder selected from transplantation rejection of organs, transplantation rejection of tissues or graft versus host diseases, in a subject, comprising administering an effective amount of a composition of 2-amino-2-(2-(4-octylphenyl)ethyl)propane-1,3-diol or a pharmaceutically acceptable acid addition salt thereof to said subject by a topical or ocular administration route.

2. A method for treating a disease or disorder selected from autoimmune diseases, inflammatory diseases, proliferative skin diseases, hyperproliferative skin diseases, or conjunctivitis in a subject comprising administering a therapeutically effective amount of a composition of 2-amino-2-(2-(4-octylphenyl)ethyl)propane-1,3-diol or a pharmaceutically acceptable acid addition salt thereof to said subject by a topical or ocular administration route.

3. A method for treating a disease or disorder selected from respiratory diseases, allergies, hepatic injury due to ischemia, inflammation of mucosa or blood vessels, renal diseases, or diseases that are caused by pathogenic organisms in a subject comprising administering an effective amount of a composition of 2-amino-2-(2-(4-octylphenyl) ethyl)propane-1,3-diol or a pharmaceutically acceptable acid addition salt thereof to said subject by a topical or ocular administration route.

4. The method according to claim 1 or 2, wherein said disease or disorder is induced from immune disorder, wherein said composition is administered via a topical administration route.

5. The method according to claim 2, wherein said disease or disorder is an eye inflammation, wherein said composition is administered in the form of an eye drop.

6. The method according to claim 1 or 2, wherein the 2-amino-2-(2-(4-octylphenyl)ethyl)propane-1,3-diol or a Pharmaceutically acceptable acid addition salt thereof is administered in combination with another immunosuppressant.

7. The method according to claim 1, wherein the other immunosuppressant is azathioprine, brequinar sodium, deoxyspergualin, mizoribine, mycophenolate 2-morpholinoethyl, cyclosporin, rapamycin, or tacrolimus monohydrate.

8. The method according to claim 7, wherein the other immunosuppressant is mycophenolate 2-morpholinoethyl, cyclosporin, or rapamycin.

9. The method according to claim 1, wherein the 2-amino-2-(2-(4-octylphenyl)ethyl)propane-1,3-diol or a pharmaceutically acceptable acid addition salt thereof is administered in combination with another immunosuppressant.

10. The method according to claim 2, wherein the 2-amino-2-(2-(4-octylphenyl)ethyl)propane-1,3-diol or a pharmaceutically acceptable acid addition salt thereof is administered in combination with another immunosuppressant.

11. The method according to claim 2, wherein the 2-amino-2-(2-(4-octylphenyl)ethyl)propane-1,3-diol or a pharmaceutically acceptable acid addition salt thereof is administered in combination with another immunosuppressant.

12. The method according to claim 5, wherein the 2-amino-2-(2-(4-octylphenyl)ethyl)propane-1,3-diol or a pharmaceutically acceptable acid addition salt thereof is administered in combination with another immunosuppressant.

13. The method according to claim 6, wherein the other immunosuppressant is azathioprine, brequinar sodium, deoxyspergualin, mizoribine, mycophenolate 2-morpholinoethyl, cyclosporin, rapamycin, or tacrolimus monohydrate.

14. The method according to claim 9, wherein the other immunosuppressant is azathioprine, brequinar sodium, deoxyspergualin, mizoribine, mycophenolate 2-morpholinoethyl, cyclosporin, rapamycin, or tacrolimus monohydrate.

15. The method according to claim 10, wherein the other immunosuppressant is azathioprine, brequinar sodium, deoxyspergualin, mizoribine, mycophenolate 2-morpholinoethyl, cyclosporin, rapamycin, or tacrolimus monohydrate.

16. The method according to claim 11, wherein the other immunosuppressant is azathioprine, brequinar sodium, deoxyspergualin, mizoribine, mycophenolate 2-morpholinoethyl, cyclosporin, rapamycin, or tacrolimus monohydrate.

17. The method according to claim 12, wherein the other immunosuppressant is azathioprine, brequinar sodium, deoxyspergualin, mizoribine, mycophenolate 2-morpholinoethyl, cyclosporin, rapamycin, or tacrolimus monohydrate.

18. The method according to claim 7, wherein the other immunosuppressant is mycophenolate 2-morpholinoethyl, cyclosporin, or rapamycin.

19. The method according to claim 14, wherein the other immunosuppressant is mycophenolate 2-morpholinoethyl, cyclosporin, or rapamycin.

20. The method according to claim 15, wherein the other immunosuppressant is mycophenolate 2-morpholinoethyl, cyclosporin, or rapamycin.

21. The method according to claim 16, wherein the other immunosuppressant is mycophenolate 2-morpholinoethyl, cyclosporin, or rapamycin.

22. The method according to claim 17, wherein the other immunosuppressant is mycophenolate 2-morpholinoethyl, cyclosporin, or rapamycin.

\* \* \* \* \*